United States Patent [19]

Nasir et al.

[11] 3,961,004
[45] June 1, 1976

[54] METHOD OF TABLETTING USING GLUCONOLACTONE AS THE DIRECT COMPRESSION DILUENT

[75] Inventors: Syed Shahid Nasir, Lahore, Pakistan; Leon Otto Wilken, Jr., Auburn, Ala.

[73] Assignee: Auburn Research Foundation, Auburn, Ala.

[22] Filed: Apr. 11, 1974

[21] Appl. No.: 459,961

[52] U.S. Cl. ............................... 264/115; 264/122; 424/279; 424/358; 424/361
[51] Int. Cl.² ................. B29B 1/032; A61K 31/365
[58] Field of Search .................... 264/122, 109, 115; 424/283, 176, 227, 279, 361, 358

[56] References Cited
UNITED STATES PATENTS

| | | |
|---|---|---|
| 3,106,512 | 10/1963 | Hill et al. .............................. 424/227 |
| 3,308,217 | 3/1967 | Lowy et al. ........................... 424/227 |
| 3,424,842 | 1/1969 | Nurnberg .............................. 264/122 |
| 3,619,292 | 11/1971 | Brouillard ............................ 264/122 |
| 3,639,168 | 2/1972 | Monti et al. ......................... 264/122 |
| 3,642,535 | 2/1972 | Graham et al. ...................... 264/122 |

*Primary Examiner*—Robert F. White
*Assistant Examiner*—James B. Lowe
*Attorney, Agent, or Firm*—Shoemaker and Mattare, Ltd.

[57] ABSTRACT

A method for producing pharmaceutical tablets, confectionary tablets or lozenges using gluconolactone in its delta or gamma lactone form as the direct compression diluent. The ingredients are mixed with gluconolactone, and then compressed directly on a tablet press without any modification in the particle size after mixing.

11 Claims, No Drawings

METHOD OF TABLETTING USING GLUCONOLACTONE AS THE DIRECT COMPRESSION DILUENT

BACKGROUND OF THE INVENTION

1. Field of the Invention

This invention relates to tablets and to a process of producing the same. More specifically, this invention relates to a direct compression diluent useful for the preparation of tablets by the "direct compression" technique.

2. Description of the Prior Art

Successful tablet making requires a material that has the proper physical shape, is dry and free flowing, possesses sufficient binding qualities to cohere when compressed and does not stick to the punches and dies of the tablet compressing machines. Some materials possess the aforementioned properties and may be directly compressed into tablets without further preparation. The vast majority of substances, however, lack one or all of these characteristics and require special preparation before compressing. Such special preparation usually consists of one or two methods or a combination thereof. These methods are commonly known in the trade as wet granulation, or granulation by the precompression or "slug" method.

The most widely used and most general method of tablet preparation is the wet granulation method. Its popularity is due to the increased probability that the granulation will meet all the physical requirements for the compression of good tablets. Its chief disadvantages are the number of steps involved, as well as the time and labor necessary to carry out the procedure, especially on a large scale. The wet method encompasses weighing, mixing and granulation of the dry powders to be tabletted. Wet granulation involves moistening the dry mixed powders by a liquid substance. The wet mass is then forced through a screen to reduce it to smaller granules which are subsequently dried until they contain a certain amount of moisture. This drying is particularly significant in the case of material which is moisture sensitive or which requires a certain optimum amount of moisture for compression. These dried granules are then passed through a final fine screen and mixed with other ingredients such as disintegrators and lubricants before compression into tablets. From the foregoing, it will be appreciated that, due to the number of steps involved, the production of tablets by the wet granulation method leaves much to be desired. It is not only time consuming, requiring a variety of equipment but also it cannot be used for materials which are decomposed by moisture and/or heat.

The second most popular method is the dry granulation process which is more efficient than the wet granulation procedure. The dry granulation process involves a fewer number of steps and hence is far more efficient than the wet granulation procedure. In this process, known as a slugging process, the powders are precompressed into flat oversized tablets or "slugs" by expensive, heavy-duty compression machines. The slugs are then crushed into granules by passing them through special machines equipped with screens. This process is time consuming as the slugging and granulation process usually has to be repeated many times before suitable granules for compression are obtained. Powder flow problems are also encountered in this process.

The process of the present invention deals with direct compression and a diluent for performing the same. The process of direct compression involves the mixing of active ingredients with a diluent and other essential ingredients of a tablet and compressing them directly on a tablet press without any modification in the particle size of the powder mixture after final blending.

Direct compression offers distinct advantages over wet granulation and slugging processes in both economics and stability of the product. In addition, a directly compressed tablet should have a faster dissolution rate and in the case of pharmaceuticals a faster drug release as a binder is not used in such a manner that it completely envelopes the particles into large and hard granules. A greater surface area is available after disintegration of tablets for dissolution due to smaller particle size. Further, due to smaller particle size, the tablet will have a more uniform appearance and there will be less wear and tear of the punches and dies since there are less compression steps and, of course, a considerable savings in time and equipment.

Although direct compression has distinct advantages it can have certain limitations and problems, particularly in the drug field. Some of these problems are the differences in particle size and bulk density between the diluent and the active ingredient may lead to stratification and variation in drug content of tablets. Further, there are problems due to poor compressibility, poor flow, nonuniform filling of dies and nonuniform blending of materials due to significant differences in particle size. There is also the problem that static charges develop on the particles during comminution and mixing which may prevent uniform distribution. In some cases there is also the problem of the drug interacting with the diluent.

All of these problems in one way or another have adverse effects on the quality of the tablets, but the three major factors are compressibility, flow and uniform die-fill of powders. These three problems can be overcome if a diluent is used in tablet formulation which improves the compression and flow properties of the mixture. There are very few known diluents with this ability, but none of them have been found to be ideal for this purpose.

Anhydrous Lactose U.S.P. and spray dried lactose are very commonly used in the direct compression of tablets since they are directly compressible and have good flow properties. A serious problem with lactose, however, is the browning reaction which is more significant in the presence of basic compounds such as amines. There is a loss of compressibility if spray dried lactose is milled or if there is moisture loss on storage. Milling also retards the flow of spray dried lactose.

Dicalcium phosphate, mannitol and sorbitol, the other directly compressible materials, have to be in moderately coarse powder, granular and crystalline form, respectively. They are non-compressible and have poor flow properties if they are in fine powder form. It has been reported that mannitol cannot be used if the concentration of the other ingredients of the tablet exceed 25% by weight. Dicalcium phosphate has good flow properties, but its capacity to compress directly is limited especially in the presence of poorly compressible materials.

Crystalline sorbitol is very hygroscopic and it lumps on storage. It cannot be milled because particle size reduction results in poor flow.

Microcrystalline cellulose is another material which is used in direct compression only as an auxiliary binder. Its relatively high cost is a deterrent factor to its use as a single diluent.

In view of the above, it has long been recognized that improvements in the conventional procedures of tabletting in the prior art are needed. It is apparent that the most desirable process for tabletting is that of direct compression and that there is a need for a diluent which does not have the inefficiencies of those used in the past but one which will have compressibility, flow, uniform die-fill and which will not react with the active ingredients.

BRIEF SUMMARY OF THE INVENTION

Objects of the Invention

It is accordingly one object of the present invention to provide a new diluent for the direct compression of tablets.

An additional object of the present invention is to provide a new diluent for the direct compression of tablets containing drugs and/or other essential ingredients, which is capable of compression even with particle size less than 30 mesh.

Another object of the invention is to provide a diluent for direct compression which is characterized by a low moisture content and which is capable of compression even after being subjected to milling.

Yet another object of the present invention resides in a novel diluent for direct compression, said diluent having no browning reaction detectable under ordinary means of detection when compressed with difficulty reactive drugs.

A further object of the invention is to provide a diluent for direct compression which will prevent stratification of a drug with which it is mixed and is capable of being present in amounts up to 89% by weight of the total composition and can contain active ingredients ranging from 0.00% to 58% of the total weight of the tablet.

A still further object of the instant invention is to provide a method of making tablets by using a sufficient amount of a novel diluent, gluconolactone, which has good dissolution rates, good stability of substances which are subject to deterioration in the presence of moisture, pleasant mouth feel and taste suitable for chewable tablets.

These and other advantages of the present invention will be apparent in the following description and examples.

In accordance with the above objects, it has been found that gluconolactone in either its delta lactone form or its gamma lactone form is an excellent diluent for aiding the tabletting of pharmaceuticals or other materials using the direct compression method. It is capable of being used with active ingredients present in the amount of 0.00% to 58% by weight of the total composition. It is also capable of being used in its commercially available form having a particle size of 80/100 mesh. A powder mixture of this diluent with drugs and/or other essential ingredients can be compressed even with particle size fine than 30-mesh and even as large as 5-mesh (US Standard), which is a definite advantage over other diluents used in direct compression methods since this avoids stratification of powder because a great difference in particle size of the various ingredients is not involved. Usually in conventional processes, a particle size ranging between 10 and 20-mesh is required. It is compressible even after being subjected to a milling process and is characterized by a low moisture content, which is favorable for moisture sensitive drugs and sugar coated tablets. It further overcomes the browning reaction which occurs with mixtures of some diluents and certain basic compounds such as amines. The diluent can be mixed with other filler materials along with active ingredients in portions as high as 89% by weight of the composition.

DESCRIPTION OF THE PREFERRED EMBODIMENTS

In accordance with the present invention there has been found a new diluent for use in direct compression of tablets. This diluent is: D-gluconic acid delta lactone or its related substance D-gluconic acid gamma lactone which are known broadly as gluconolactone. Gluconolactone is a sweet crystalline powder highly soluble in water (59 gm/100 ml) which is easily synthesized. One method of producing gluconolactone is by the oxidation of glucose in the presence of bromine water. The product, however, is available on the market and is capable of being used in its commercially available form of 80/100-mesh particle size. This small particle size will prevent stratification of the drugs from the mixed powders. One source is glucono delta lactone produced by I.C.N. Nutritional Biochemicals Corporation of Cleveland, Ohio. Experiments have shown that this material due to its unique properties, overcome most of the tabletting problems associated with other direct compression diluents known in the prior art. This material does not lose its compressibility even on milling. It contains only 0.5% moisture which is a favorable advantage because high moisture content will lead to deterioration of moisture sensitive drugs and increase the rate of those chemical and physical reactions accelerated by the presence of moisture. A 6 month storage of plain gluconolactone tablets at room temperature did not show any indication of browning reaction. It is effective in direct compression of even poorly compressible materials such as amino salicyclic acid up to 48% of the total tablet weight, calcium lactate up to 48.5% and ascorbic acid up to 47% of the total tablet weight.

A comparative study was conducted concerning the stability of acetyl salicylic acid with various diluents. Separate mixtures containing equivalent amounts of acetyl salicylic acid with gluconolactone, mannitol and sorbitol, anhydrous lactose and spray dried lactose, respectively, were stored at high and moderate humidities and room temperature for specified periods of time. The results of this study indicated that the degree of hydrolysis of the acid in the presence of gluconolactone was significantly less as compared to the other directly compressible diluents studied.

The ability of gluconolactone to aid in direct compression of tablets was studied with a variety of drugs having different physical and chemical properties. Plain tablets of gluconolactone were also prepared in this study. In all cases, glluconolactone was passed through a 30-mesh screen and then mixed with the drugs and other additives which were also passed through a 30-mesh screen. The gluconolactone had the following particle size distribution on passing through U.S. standard sieves:

| Mesh Size | % Retained |
|-----------|------------|
| 20 | 0.03 |
| 30 | 4.51 |
| 40 | 5.78 |
| 60 | 6.67 |
| 80 | 9.03 |
| 100 | 74.01 |

All mixed powders were tabletted on Colton four-station rotary press at a speed of 300 tablets per minute using various sizes and types of punches and dies, with the exception of Riboflavin and multivitamin tablets which were compressed on Stokes Model F-3 single punch press at a speed of 60 tablets per minute.

EXAMPLE I

Plain Gluconolactone Tablets

Gluconolactone 79%
Methy cellulose 1500 cps 10%
Dried starch 10%
Magnesium stearate 1%
Punches and dies ⅜ inch deep concave
Hardness 6.67 ± 0.83 kg stokes
Thickness 5.63 ± 0.83 mm
Weight 628 ± 9.52 mg Disintegration Time Water at 37° 2.22 ± 0.23 min.
Simulated Gastric Fluid USP at 37° 2.13 ± 0.56 min.
Simulated Intestinal Fluid USP at 37° 6.01 ± 0.42 min.

EXAMPLE II

Plain Gluconolactone Tablets

Gluconolactone 89%
Methyl cellulose 1500 cps 10%
Magnesium stearate 1%
Punches and dies 7/16 inch standard concave
Hardness 8.7 ± 0.10 kg stokes
Thickness 6.5 ± 0.057 mm
Weight 630 ± 16.57 mg Disintregration Time Water at 37° 3.55 ± 0.33 min.
Simulated Gastric Fluid USP at 37° 6.57 ± 1.26 min.
Simulated Intestinal Fluid USP at 37° 6.91 ± 0.73 min.

EXAMPLE III

Plain Gluconolactone Tablets

Gluconolactone 89%
Methyl cellulose 1500 cps 5%
Starch 5%
Magnesium stearate 1%
Punches and dies 7/16 inch standard concave
Hardness 6.04 ± 0.85 kg stokes
Thickness 5.6 ± 0.0577 mm
Weight 623 ± 6.57 mg Disintegration Time Water at 37° 4.17 ± 0.43 min.
Simulated Gastric Fluid USP at 37° 3.69 ± 0.29 min.
Simulated Intestinal Fluid USP at 37° 4.29 ± 0.218 min.

EXAMPLE IV

Ferrous Sulfate Tablets

Ferrous sulfate anhydrous powder 149 mg
Gluconolactone 360 mg
Methyl cellulose 1500 cps 40 mg.
Magnesium stearate 11.0 mg
Punches and dies ⅜ inch deep concave
Hardness 5.15 ± 0.657 kg stokes
Thickness 5.5 ± 0.033 mm
Weight 559 ± 9.23 mg
Disintegration time in water at 37° 9.3 ± 0.81 min.

EXAMPLE V

Phenobarbital Tablets

Phenobarbital 30 mg
Gluconolactone 160 mg
Methyl cellulose 1500 cps 40 mg
Magnesium stearate 1.25 mg
Stearic acid 3.75 mg
Punches and dies 5/16 inch standard concave
Hardness 6.4 ± 0.917 kg stokes
Thickness 4.1 ± 0.00 mm
Weight 243 ± 9.24 mg
Disintegration time in water at 37° 6.03 ± 1.28 min.

EXAMPLE VI

Sodium Chloride Tablets

Sodium chloride 600 mg
Gluconolactone 540 mg
Methyl cellulose 60 mg
Magnesium stearate 12 mg
Punches and dies ½ inch flat faced beveled edge
Hardness 5.2 ± 0.341 kg stokes
Thickness 6.26 ± 0.0515 mm
Weight 1211 ± 36.2 mg
Disintegration time in water at 37° 6.28 ± 0.35 min.

EXAMPLE VII

Ephedrine Hydrochloride Tablets

Ephedrine hydrochloride 30 mg
Gluconolactone 135 mg
Methyl cellulose 1500 cps 15 mg
Stearic acid 3.0 mg
Magnesium stearate 2.0 mg
Punches and dies 5/16 inch standard concave
Hardness 4.6 ± 1.22 kg stokes
Thickness 3.62 ± 0.103 mm
Weight 194.5 ± 20 mg.
Disintegration time in water at 37° 11.3 ± 0.18 min.

EXAMPLE VIII

Isoniazid Tablets

Isoniazid 50 mg
Gluconolactone 260 mg
Methyl cellulose 1500 cps 40 mg
Magnesium stearate 7 mg
Punches and dies 5/16 inch standard concave
Hardness 5.25 ± 0.485 kg stokes
Thickness 5.45 ± 0.0971 mm
Weight 354 ± 7.24 mg
Disintegration time in water at 37° 8.32 ± 0.50 min.

EXAMPLE IX

Methenamine Tablets

Methenamine 250 mg
Gluconolactone 150 mg
Methyl cellulose 1500 cps 25 mg
Magnesium stearate 4.4 mg
Stearic acid 8.6 mg Punches and dies 7/16 inch standard concave
Hardness 6.15 ± 0.885 kg stokes
Thickness 4.64 ± 0.0966 mm
Weight 445 ± 11.0 mg
Disintegration time in water at 37° 6.25 ± 0.78 min.

EXAMPLE X

Ascorbic Acid Tablets

Ascorbic acid powder 300 mg
Gluconolactone 240 mg
Methyl cellulose 80 mg
Magnesium stearate 6 mg
Stearic acid 12 mg
Punches and dies 7/16 inch standard concave
Hardness 6.55 ± 1.26 kg stokes
Thickness 6.64 ± 0.135 mm
Weight 633 ± 14.8 mg
Disintegration time in water at 37° 16.0 ± 0.00 min.

EXAMPLE XI

Sulfathiazole Tablets

Sulfathiazole 500 mg
Gluconolactone 360 mg
Methyl cellulose 45 mg
Starch 45 mg
Magnesium stearate 4.8 mg
Stearic acid 19.2 mg
Punches and dies ½ inch flat faced beveled edge
Hardness 6.8 ± 0.889 kg stokes
Thickness 5.9 ± 0.087 mm
Weight 967 ± 22.17
Disintegration time in water at 37° 25 ± 4.73 min.

EXAMPLE XII

Ferrous Gluconate Tablets

Ferrous gluconate 300 mg
Gluconolactone 270 mg
Methyl cellulose 30 mg
Magnesium stearate 6 mg
Stearic acid 12 mg
Punches and dies 7/16 inch standard concave
Hardness 11.0 ± 1.8 kg stokes
Thickness 5.9 ± 0.1 mm
Weight 627 ± 10.15 mg
Disintegration time in water a 37° 9.77 ± 3.47 min.

EXAMPLE XIII

Calcium Lactate Tablets

Calcium lactate 300 mg
Gluconolactone 240 mg
Methyl cellulose 1500 cps 60 mg
Magnesium stearate 6 mg
Stearic acid 12 mg
Punches and dies 7/16 inch standard concave
Hardness 13.3 ± 1.26 kg stokes
Thickness 6.5 ± 0.124 mm
Weight 616 ± 20.28 mg
Disintegration time in water at 37° 15.60 ± 3.215 min.

EXAMPLE XIV

Aspirin Tablets

Acetyl salicylic acid 150 mg
Gluconolactone 360 mg
Methyl cellulose 1500 cps 40 mg
Starch 40 mg
Magnesium stearate 6 mg
Punches and dies 7/16 inch standard concave
Hardness 5.5 ± 0.687 kg stokes
Thickness 5.7 ± 0.141 mm
Weight 607 ± 19.09 mg
Disintegration time in water at 37° C 3.88 ± 0.799

EXAMPLE XV

Riboflavin Tablets

Riboflavin 5 mg
Gluconolactone 90 mg
Methyl cellulose 1500 cps 10 mg
Magnesium stearate 1 mg
Punches and dies ¼ inch deep concave
Hardness 2.4 ± 0.394 kg stokes
Thickness 3.37 ± 0.105 mm
Weight 108 ± 2.9 mg
Disintegration time in water at 37° 5.38 ± 0.56 min.

EXAMPLE XVI

Multivitamin and Mineral Tablets

Vitamin A. 5000 USP units
Vitamin D 400 USP units
Thiamine 2 mg
Riboflavin 3 mg
Niacinamide 20 mg
Ascorbic acid 50 mg
Pyridoxine 1 mg
Cyanocobalamine 1 mcg
Calcium pentothenate 1 mg
Ferrous sulfate 18 mg
Copper sulfate 1 mg
Magnesium oxide 5 mg
Manganese citrate 1 mg
Zinc chloride 1.5 mg
Gluconolactone 180 mg
Methyl cellulose 1500 cps 20 mg
Magnesium stearate 3 mg
Stearic acid 6 mg
Punches and dies 3/8 inch deep concave
Hardness 4.95 ± 1.01 kg stokes
Thickness 4.38 ± 0.103 mm
Weight 312 ± 5.0 mg
Disintegration time in water at 37° 5.78 ± 1.60 min.

EXAMPLE XVII

Amino Salicylic Acid Tablets

Amino salicylic acid 250 mg
Gluconolactone 320 mg
Methyl cellulose 1500 cps 80 mg
Magnesium stearate 6 mg
Stearic acid 14 mg
Punches and dies 7/16 inch standard concave
Hardness 6.55 ± 1.26 kg stokes
Thickness 6.64 ± 0.135 mm
Weight 700 ± 22.9 mg
Disintegration time in water at 37° 16.0 ± 1.5 min.

Having thus described the compositions of the invention in terms of their preferred embodiments as set forth in the description and the examples of the aforesaid specification, it is apparent to those skilled in the art that various changes and modifications can be made in the composition without departing from the scope of the invention. Thus, for example, it is possible for the direct compression method to be used for producing pharmaceutical tablets, confections, lozenges, etc.

What is claimed is:

1. In a method for producing a tablet selected from the group consisting of pharmaceutical, confectionary, and lozenge by the direct compression method consisting essentially of mixing the ingredients with a compression diluent and compressing said ingredients and diluent directly on a tablet press without any modification in the particle size after mixing wherein the improvement is using gluconolactone in an amount sufficient to act as the direct compression diluent by itself.

2. The method of claim 1 wherein the gluconolactone is selected from the group consisting of D-gluconic acid delta lactone, D-gluconic acid gamma lactone.

3. The method of claim 1 wherein the gluconolactone is used in its commercially available form.

4. The method of claim 1 wherein the gluconolactone is present in an amount up to about 89% by weight of the total composition.

5. The method of claim 1 wherein the ingredients contain an active ingredient in an amount of 0.00% to 58% by weight of the total composition.

6. The method of claim 1 wherein the gluconolactone is of a mesh size of 80/100-mesh.

7. The method of claim 1 wherein the diluent and ingredients are compressible with particle size finer than 5-mesh.

8. The method of claim 1 wherein the mesh size of the gluconolactone is less than 30-mesh.

9. The method of claim 1 wherein there is contained at least 11% of at least one member selected from the group consisting of binders, lubricants, flavoring material and active ingredient.

10. The method of claim 1 wherein the gluconolactone is milled prior to mixing.

11. The method of claim 1 wherein the gluconolactone has a moisture content of 0.5%.

* * * * *